United States Patent [19]

Eggimann et al.

[11] Patent Number: 4,716,219

[45] Date of Patent: Dec. 29, 1987

[54] ADSORBENT FOR PROTEIN PURIFICATION

[75] Inventors: Bernhard Eggimann, Basel; Erich Hochuli, Arisdorf; Alfred Schacher, Riehen, all of Switzerland

[73] Assignee: Hoffmann-La Roche Inc., Nutley, N.J.

[21] Appl. No.: 821,728

[22] Filed: Jan. 23, 1986

[30] Foreign Application Priority Data

Feb. 4, 1985 [CH] Switzerland .................. 490/85

[51] Int. Cl.$^4$ .................................................. C07K 3/20
[52] U.S. Cl. ................................. 530/413; 530/412; 530/417; 530/351; 424/85; 435/178; 435/180; 435/181; 435/811; 536/123; 536/1.1; 536/55.1; 436/528; 436/529; 436/531; 436/532; 525/329.4; 525/384; 525/385
[58] Field of Search ............... 530/351, 412, 417, 413; 424/85; 536/123, 1.1; 436/528-529, 531-532; 435/178, 180-181; 525/329.4, 384, 385

[56] References Cited

U.S. PATENT DOCUMENTS

| | | | |
|---|---|---|---|
| 4,172,071 | 10/1979 | Maeyers et al. | 424/85 |
| 4,278,617 | 7/1981 | Knight | 424/85 |
| 424,278,661 | 7/1981 | Knight | 424/85 |
| 4,286,964 | 9/1981 | Seed | 436/532 |
| 4,289,689 | 9/1981 | Friesen et al. | 424/85 |
| 4,382,027 | 5/1983 | Braude | 424/85 |
| 4,541,952 | 9/1985 | Hosoi et al. | 424/85 |
| 4,546,161 | 10/1985 | Harvey et al. | 436/528 |

FOREIGN PATENT DOCUMENTS 0257836 12/1985 Japan .

OTHER PUBLICATIONS

Parikh et al., *C & EN New* 1985, pp. 17–32.
Dye Ligand Chromatography *Amicon;* 1980.
Averameas et al., C.A. vol. 72, 1970, #63566w.
Jakoby et al., *Methods Enzymol.* vol. 34, 1974, pp. 24–27.
Lowe et al., *Int. J. Biochem.* 13, 1981, pp. 33–40.
Dean et al., *J. Chromatography* 165, 301–319 (1979).
Staehelin et al., *J. Biol. Chemistry* 256, 9750–9754 (1981).
Berg et al., *Scand. J. Immunol.* 8, 429–436 (1978).

*Primary Examiner*—Morton Foelak
*Assistant Examiner*—Garnette D. Draper
*Attorney, Agent, or Firm*—Jon S. Saxe; George M. Gould; Norman C. Dulak

[57] ABSTRACT

Adsorbents, which are suitable for the affinity chromatography of proteins, especially of interferons, and which consist of an electroneutral carrier matrix, —O—CH$_2$—CH(OH)—CH$_2$—NH— groups as the spacer and a triazine coloring substance bonded to the spacer.

13 Claims, No Drawings

ADSORBENT FOR PROTEIN PURIFICATION

BACKGROUND OF THE INVENTION

In the purification of proteins, for example of interferons, by affinity chromatography there are already used adsorbents which consist of a carrier matrix, for example agarose, cross-linked dextrans or polyacrylamides, to which are directly covalently bonded as reactive groups colouring substances, especially triazine colouring substances such as the previously named (J. Chromatog. 165, 301 [1979]. Dean et al.), or antibodies which are specific for the proteins to be purified. Such adsorbents, which are suitable e.g. for the purification of interferon, are described, for example, in U.S. Pat. Nos. 4,172,071 (De Maeyer et al.), 4,278,661 (Knight, Jr.) and 4,289,689 (Friesen et al.), as well as in J. Biol. Chem. 256, 9750 [1981] (Staehelin et al.) and Scand. J. Immunol. 8, 429 [1978] (Berg et al.).

SUMMARY OF THE INVENTION

The present invention is concerned with novel resins, or adsorbents, which are suitable for affinity chromatography and which accordingly can be used for the purification of proteins, especially of interferons, as well as with a process for the purification of proteins, especially interferons, by means of these novel resins.

The resins in accordance with the invention consist of an electroneutral carrier matrix, —O—CH$_2$—CH(OH)—CH$_2$—NH groups as the spacer and a triazine colouring substance as the reactive ligand bonded to the spacer amino group.

As the electroneutral carrier matrix there come into consideration materials which are used in affinity chromatography and gel chromatography, such as cross-linked dextrans, agarose (especially in the form which is known under the trade mark Sepharose ®) or polyacrylamides.

As the triazine colouring substance there come into consideration the reactive colouring substances, such as those belonging to the reactive blue and reactive red group, which are already known from affinity chromatography, numbered among which are the best-known representatives Cibacron ® Blue, Cibacron ® Brilliant Red and Procion ® Red (see e.g. Int. J. Biochem. 13, 33–40 [1981] and J. Chromatog. 165, 301–319 [1979]) and which are commercially obtainable.

The structures of the above dyes are as follows:

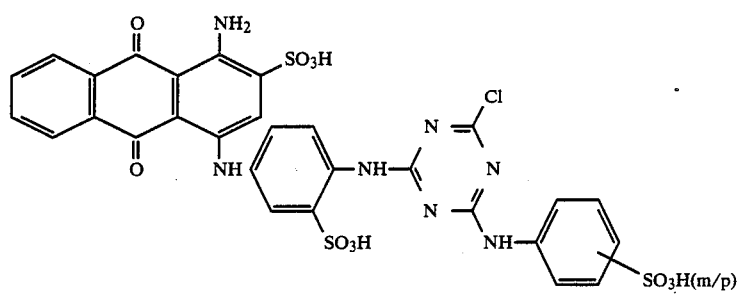

Cibacron ® Blue

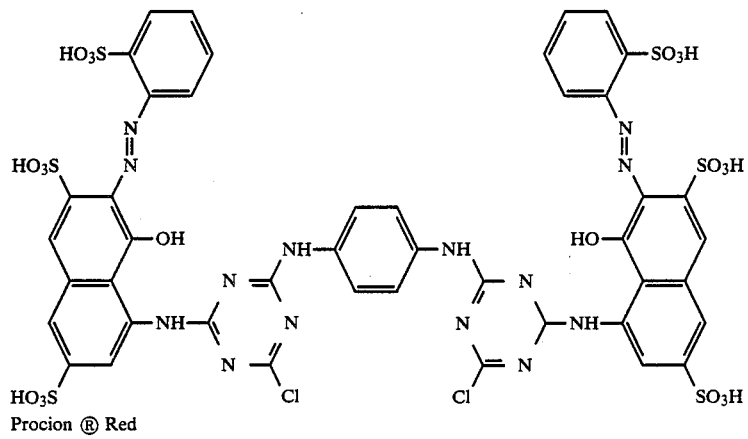

Procion ® Red

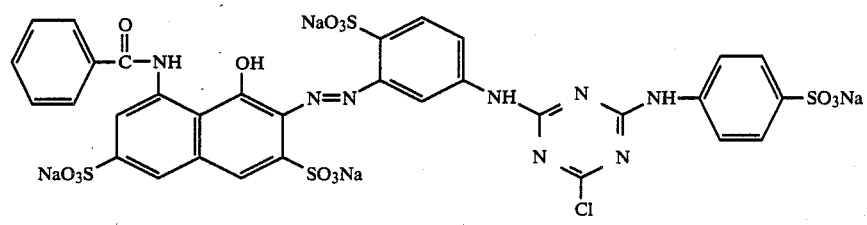

Cibacron ® Brilliant Red

The adsorbents in accordance with the invention are distinguished vis-a-vis the known adsorbents primarily in that they have a mechanically larger loading capacity and higher flow rates than the comparable known resins such as e.g. Blue Sepharose ®, which makes them especially suitable for use on an industrial scale. This advantage is especially critical when buffers having a high salt concentration or buffer mixtures from organic solvents and aqueous salt solutions having a high viscosity are used for the chromatography.

It has been shown that the resins in accordance with the invention are distinguished by an especially high specificity to β-interferon (fibroblast interferon) and are accordingly particularly suitable for the purification of β-interferon and its analogues, especially of recombinant β-interferon. However, over and above this, on the basis of their advantageous properties they are suitable not only for the purification of other interferons (α, γ-, hybrid interferons) or lymphokines, such as interleukin-2, of different origin, but also of proteins quite generally, in which case, depending on the product, the choice of the most suitable carrier matrix as well as of the reactive ligand and the optimization of the process conditions can be effected in the scope of the general knowledge of the person skilled in the art. Of course, the resins can be used batch-wise or in columns which are to be operated continuously.

DESCRIPTION OF THE PREFERRED EMBODIMENT

The manufacture of the adsorbents in accordance with the invention can be carried out in a manner known per se, with the matrix being firstly functionalized (introduction of the spacer) and then the desired colouring substance being covalently bonded via the spacer. When agarose is used as the starting material, it is reacted, for example, with epibromohydrin in an alkaline medium and the epoxide ring is opened by reaction with aqueous ammonia so that 3-amino-2-hydroxypropyl-agarose is obtained (see J. Solid-Phase Biochem. 1, 33 [1976]). After the reaction with the desired colouring substance excess free spacer-3-amino functions can be blocked, for example, by reaction with potassium cyanate (conversion into ureido groups). Polyacrylic resins which contain free hydroxyl groups can be converted into adsorbents in accordance with the invention in an analogous manner.

A starting material for a preferred resin type in accordance with the invention based on a polyacrylamide carrier matrix is an oxirane-polyacrylic resin which contains

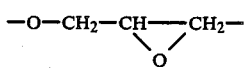

groups and which is marketed under the brand name Eupergit ®-C of the firm Röhm Pharma GmbH, Darmstadt. The epoxypropyl groups of Eupergit ®-C can be converted into 3-amino-2-hydroxypropyl groups by treatment with aqueous ammonia. Aminoeupergit which is thus-obtained can then be converted into the desired resin in accordance with the invention in a manner known per se by reaction with a reactive colouring substance, as indicated previously.

Especially preferred reactive colouring substances in connection with the present invention are Cibacron ® Blue 3G-A or F3G-A and Cibacron ® Brilliant Red 4G-E.

The following Examples illustrate the manufacture of some adsorbents in accordance with the invention as well as their use in the purifications of recombinant human fibroblast interferon (rIFN-β), whereby the relative proportions of the reaction partners are not critical and can be varied depending on the problem posed, i.e. depending on the protein or protein mixture to be purified. In this manner there can be obtained adsorbents in accordance with the invention which differ from one another in spacer or colouring substance content. The optimal proportions can be readily determined empirically by the person skilled in the art. For the purification of fibroblast interferon (IFN-β) an amount of about 7-8 μmol of Cibacron ® Blue per ml of gel has, for example, been shown to be very favourable, but from about 2 to up to about 15 μmol of colouring substance can be used.

The purification of proteins with the resins in accordance with the invention can be carried out analogously to the chromatography of natural fibroblast interferon from human tissue on Blue Dextran Sepharose ® which is described by Friesen et al (Arch. Biochem. Biophys. 206, 432–450 [1981]).

The rIFN-β crude extract used as the starting material was prepared according to the method of Goeddel et al. (Nucleic Acids Res. 8, 4057–4074 [1980]).

The elution was followed with a photometer having a flow cell (wavelength 280 nm) and a recorder. The eluates were collected with the aid of a fraction collector and fractionated.

The pure interferon solution obtained can be dialyzed against 0.05M sodium acetate buffer in order to remove the ethylene glycol and can be concentrated by ultrafiltration.

The determination of the protein content was carried out according to the method of Lowry et at. (J. Biol. Chem. 193, 265–275 [1951]) using serum albumin as the standard.

The purity determination was carried out by means of SDS-PAGE as described by Laemmli et al. (Nature 277, 680–685 [1970]), with the modification that the electrophoresis was carried out under non-reducing conditions (i.e. without the addition of 2-mercaptoethanol). As the protein standard marker there was used a mixture of lysozyme (MW: 14,400), trypsin inhibitor (MW: 21,500), carbonil anhydrase (MW: 31,000), ovalbumin (MW: 45,000), bovine serum albumin (MW: 66,200) and phosphorylase B (MW: 92,500).

EXAMPLE 1

Manufacture of an agarose-Cibacron ® Blue resin 50 ml of agarose gel (Sepharose ® CL-6B) were washed twice on a glass suction filter with about 250 ml of water, transferred into a 200 ml sulphonation flask and brought to a volume of 100 ml with water. After the addition of 8 ml of 4N NaOH and 2 ml of epibromohydrin the mixture was stirred at 30° C. for 5 hours. The activated resin was washed neutral on the suction filter with water and transferred back into the sulphonation flask. After the addition of 100 ml of 5% ammonia solution (wt./vol.%) the mixture was stirred at room temperature overnight. The resin was then again washed neutral and brought to a volume of 100 ml with water. After the addition of 1 g of $Na_2CO_3$ and 271 mg of Cibacron ® BLue 3G-A (7 μmol/ml of gel) the mixture was stirred at 50° C. for 20 hours. The finished gel was washed colourless on the glass suction filter in sequence with in each case about 500 ml of water, methanol/water (1:1) and water.

EXAMPLE 2

Manufacture of an aminoeupergit-Cibacron ® Blue resin 250 ml of 5% ammonia solution (wt./vol.%) were placed in a 500 ml round flask. After 25 g of Eupergit ® C had been added portionwise the mixture was stirred slowly with a paddle stirrer at room temperature for 6 hours. The stirring was then stopped and the supernatant was sucked off after three minutes. The resin was again suspended with 100 ml of water and after 3 minutes the supernatant was again sucked off. This procedure was repeated four times. The thus-obtained moist aminoeupergit was transferred into a 500 ml 4-necked flask, treated with 200 ml of 0.2M disodium hydrogen phosphate and 688 mg of Cibacron ® Blue 3G-A (8 $\mu$mol per ml of gel) and stirred slowly at 40° C. for 20 hours. The resin was then washed on a glass suction filter in sequence with in each case 500 ml of water, 0.01N hydrochloric acid and water. The gel was subsequently transferred back into the reaction vessel, treated with 220 ml of water and 2.08 g of potassium cyanate and stirred slowly at room temperature for 15 hours. The finished resin (about 100 ml) was finally washed on the glass suction filter in sequence with in each case 1:1 of water, methanol/water (1:1) and water.

EXAMPLE 3

Manufacture of an aminoeupergit-Cibacron ® Brilliant Red resin 100 ml of aminoeupergit, prepared from 25 g of Eupergit ® C according to the method described in Example 2, were treated in a 500 ml flask with 200 ml of 0.2M disodium hydrogen phosphate and 1.029 g of Cibacron ® Brilliant Red 4G-E (7 $\mu$mol of colouring substance per ml of gel). The reaction mixture was stirred slowly at 40° C. for 15 hours. The resin was subsequently washed on the suction filter in sequence with in each case 500 ml of water, 1M potassium chloride solution, 0.01N hydrochloric acid and again with water.

The resin was then returned to the reaction flask and stirred for about 15 hours in 200 ml of water with 2.08 g of potassium cyanate. The ready-for-use resin (about 100 ml) was washed with water, methanol/water and again with water in a manner analogous to Example 2.

EXAMPLE 4

Purification of rIFN-$\beta$ on an agarose-Cibacron ® Blue resin

A column (2.6×4.7 cm ), containing 25 ml of the agarose-Cibacron ® Blue resin manufactured in accordance with Example 1, was equilibrated with about 200 ml of 0.05M phosphate buffer (pH 7.2, 1M NaCl). The column was loaded at 4° C. with 1050 ml of rIFN-$\beta$ crude extract, obtained from 28 g of deep-frozen E. coli cells in accordance with Goeddel et al. (Nucleic Acids Res. 8, 4057 [1980]), with a flow rate of 8 cm/hour (ml/cm$^2$/hr.). The column was subsequently washed at room temperature in succession with in each case 100 ml of phosphate buffer (0.05M, pH 7.2, 1M NaCl) containing 15 and 30 vol./vol.%, respectively, of ethylene glycol and the interferon was eluted with phosphate buffer (0.05M, pH 7.2, 1M NaCl) containing 50 vol.-/vol.% of ethylene glycol. There were obtained 2.2 mg of pure rIFN-$\beta$ (purity >95% in accordance with SDS-PAGE) in 66 ml of elution buffer.

Subsequently, the column was made ready for use again by washing with phosphate buffer (0.05M, pH 7.2, 1M NaCl) containing 70 vol./vol.% of ethylene glycol.

EXAMPLE 5

Purification of rIFN-$\beta$ on an aminoeupergit-Cibacron ® Blue resin (a) A column (2.6×7 cm), containing 37 ml of the aminoeupergit-Cibacron ® Blue resin manufactured in accordance with Example 2, was equilibrated with about 200 ml of 0.05M phosphate buffer (pH 7.2, 1M NaCl). The column was then loaded at 6° C. with 700 ml of rIFN-$\beta$ crude extract, obtained from 14.8 g of deep-frozen E. coli cells in accordance with Goeddel et al. (Nucleic Acids Res. 8, 4057 [1980]), at a flow rate of 38 cm/hr. The column was subsequently washed at room temperature in succession with 130 ml of phosphate buffer (0.05M, pH 7.2, 1M NaCl) containing 15 and 30 vol./vol.%, respectively, of ethylene glycol as well as with 60 ml of phosphate buffer (0.05M, pH 7.2, 1M NaCl) containing 30 vol./vol.% of ethylene glycol and the interferon was eluted with phosphate buffer (0.05M, pH 7.2, 1M NaCl) containing 50 vol./vol.% of ethylene glycol. There were obtained 1.15 mg of pure rIFN-$\beta$ (purity >95% in accordance with SDS-PAGE) in 38 ml of elution buffer.

Subsequently, the column was made ready for use again by washing with phosphate buffer (0.05M, pH 7.2, 1M NaCl) containing 70 vol./vol.% of ethylene glycol.

(b) In a manner analogous to (a), a column (14×13 cm). containing 2 l of the resin manufactured in accordance with Example 2, was loaded with 60 l of rIFN-$\beta$ crude extract, obtained from 2 kg of E. coli cells (in accordance with Goeddel et al.), at a flow rate of 39 cm/hour, washed and eluted, whereby 300 mg of pure rIFN-$\beta$ (purity >95% in accordance with SDS-PAGE) in 2.3 l of elution buffer were obtained.

We claim:

1. An adsorbent comprising an electroneutral carrier matrix, —O—CH$_2$—CH(OH)—CH$_2$—NH— groups as a spacer and a triazine colouring substance bonded to the spacer, which adsorbent is characterized by providing high flow rates and a large loading capacity.

2. An adsorbent in accordance with claim 1, wherein the carrier matrix is agarose.

3. An adsorbent in accordance with claim 1, wherein the carrier matrix is a polyacrylamide resin.

4. An adsorbent in accordance with any one of claims 1-3, wherein the triazine colouring substance is selected from the group consisting of Cibacron ® Blue and Cibaron ® Brilliant Red.

5. An adsorbent in accordance with one of claims 1, 2 or 4, wherein Cibacron ® Blue is bonded to agarose via —O—CH$_2$—CH(OH)—CH$_2$—NH— groups.

6. An adsorbent in accordance with one of claims 1, 3 or 4, wherein Cibacron ® Blue is bonded to aminoeupergit.

7. An adsorbent in accordance with one of claims 1, 3 or 4, wherein Cibacron ® Brilliant Red is bonded to aminoeupergit.

8. A process for the manufacture of an adsorbent for affinity chromatography, which process comprises reacting a matrix functionalized with 3-amino-2-hydroxypropyl groups with a triazine colouring substance.

9. A process in accordance with claim 8, wherein aminoeupergit is reacted with Cibacron ® Blue or Cibacron ® Brilliant Red.

10. A process for the purification of proteins, which process comprises subjecting them to affinity chromatography on an adsorbent in accordance with claim 1.

11. A process in accordance with claim 10, wherein an interferon solution is subjected to affinity chromatography.

12. A process in accordance with claim 11, wherein a solution of recombinant fibroblast interferon is subjected to affinity chromatography.

13. The process of claim 8 in which any excess free 3-amino functions are blocked by reaction with potassium cyanate.

* * * * *